United States Patent
Koblanski

Patent Number: 6,022,318
Date of Patent: Feb. 8, 2000

[54] ULTRASONIC SCANNING APPARATUS

[76] Inventor: John N. Koblanski, 1205-4160 Sardis Street, Burnaby, Canada, V5H 1K2

[21] Appl. No.: 08/607,331

[22] Filed: Feb. 26, 1996

[51] Int. Cl.$^7$ ........................................................ A61B 8/00
[52] U.S. Cl. ............................................................ 600/449
[58] Field of Search ................................... 600/437–438, 600/443, 449, 459; 73/632, 644

[56] References Cited

U.S. PATENT DOCUMENTS

| | | | |
|---|---|---|---|
| 4,211,949 | 7/1980 | Brisken et al. | 600/459 X |
| 4,365,515 | 12/1982 | Abts | 73/632 |
| 5,452,722 | 9/1995 | Langton | 600/449 |
| 5,505,205 | 4/1996 | Solomon et al. | 600/459 |

*Primary Examiner*—Francis J. Jaworski
*Attorney, Agent, or Firm*—Daniel L. Dawes

[57] ABSTRACT

Apparatus to measure the physical characteristic of an object. There is a main body to receive the object. There is a device to enable the operator to determine when the object is correctly on the body. A piezoelectric ultrasonic transmitter sends a signal through the object. The transmitter comprise a first hollow container slidably received in the main body and a piezoelectric ceramic transmitter resiliently mounted in the first container. Transmitter is urged towards the object but its movement is restricted. A piezoelectric ultrasonic receiver spaced from the transmitter also projects towards the body. The receiver comprise a second hollow container slidably received in the main body. A ceramic transducer is resiliently mounted in the second hollow container. A signal is generated to be transmitted. The signal can be amplified. In a preferred embodiment the object is a foot and the device is useful in determining the presence of a osteoporosis. A method of measuring the physical characteristic of an object is described. The object is subjected to resonating frequencies in the same piezoelectric ultrasonic transmitter. A first resonating frequency obtained by resonating the thickness mode is obtained and the second lower resonating frequency obtained by resonating the radial mode is obtained. From these measurements the physical characteristics of the object can be deduced.

17 Claims, 7 Drawing Sheets

ULTRASONIC SCANNING APPARATUS

FIELD OF THE INVENTION

This invention relates to an apparatus and to a method to measure the physical characteristics of an object. The apparatus and method find particular application measuring the physical characteristics of bone and is thus of value in diagnosing osteoporosis and osteomalacia. However the invention finds general application in assessing the structural properties of materials and in detecting minute changes in that structure. Although this is of particular value in determining the integrity of heterogenous materials such as bone, the invention, in both aspects, is of wider application.

BACKGROUND OF THE INVENTION

Osteoporosis is a condition, more common amongst women than men, characterized by deterioration of the bone. The bone becomes porous and brittle. Osteoporosis at present is diagnosed by measuring the density and elasticity of the bone. High density alone does not determine the bone resistance to fracture. The bone can possess quite high density but still be brittle and therefore susceptible to breakage. Prior art methods of measuring bone density do not have the required degree of accuracy to determine small changes in bone density, which is what is needed to establish optimum therapeutic or diagnostic procedures.

Osteomalacia is a condition in which softening of the bone occurs. Softening is the result of absorption of calcium from the bones. It occurs especially in pregnant women and it is believed to be related to a dietary deficiency in vitamin D.

My co-pending U.S. patent application Ser. No. 018,709 filed Feb. 17, 1993 describes and claims an apparatus to measure the physical characteristic of an object. The apparatus has a bath to receive the object and the object can be stabilized in the bath. Liquid is supplied to and from the bath. The temperature of the liquid can be controlled so that it is above the temperature of the object. An ultrasonic transmitter sends a signal through the object and an ultrasonic receiver receives the signal. The velocity of the signal of the object can be calculated. This apparatus is useful in diagnosing osteoporosis.

The heel bone is suited to ultrasonic measurement with its sides relatively parallel. The heel bone is composed mainly of trabecular bone. The elasticity and strength of this bone is provided by its sheet structure. The manner in which trabeculae are assembled is more significant than the volume or any other characteristic of bone. Rigidity and strength is more a matter of geometry than mass. The trabeculae arrangement, and the contiguity that it provides, is a more important parameter than volume or weight for action of hard tissue in determining the stiffness of trabecular bone. Because of these facts the known methods of utilizing the velocity of sound in bone and the attenuation measurements, although appearing to provide sound theoretical methods, have not been satisfactory in diagnosing osteoporosis and are not capable of evaluating the effectiveness of any treatment procedure.

Another difficulty with existing methods is their dependence upon references or standards. Using the standards creates an additive error to any measurement. In addition to this error, the use of standards having homogenous composition is undesirable as these compositions relate poorly to human bone; human bone is a heterogenous material.

X-ray methods have been used to diagnose osteoporosis but have also been found unsatisfactory. They measure only the density and provide no quantitative evaluation of structure. Because they produce ionizing radiation, X-rays are not suitable for this purpose.

No prior art has shown an ability to measure bone structure, density and the velocity of sound in bone using a single device. The use of a single device provides a means of early detection as well as a more accurate assessment of the degree of osteoporosis.

All the present methods depend highly on instrument electronic stability. This can be undesirable. There can also be a lack of uniformity in the transducer characteristic, stemming from the manufacturing process.

Furthermore the accuracy with which the heel can be re-positioned for repeat measurements is not particularly satisfactory in the prior art. The reapplying of the transducer against the heel with the same conditions, particularly the same contact pressure, for subsequent measurements is also not well done in the prior art.

SUMMARY OF THE INVENTION

The present invention seeks to avoid the disadvantages in the prior art. In particular the present invention allows for instrumental base line drift without the introduction of errors into the measurement. The invention also provides for extremely accurate location of the heel and easy repetition of the location of the heel for subsequent measurements.

A particular advantage of the present invention is that it is self-calibrating.

Accordingly, in its apparatus aspect, the present invention provides an apparatus to measure the physical characteristic of an object comprising:

a main body to receive the object;

means to determine when the object is correctly on the body;

a piezoelectric ultrasonic transmitter to send a signal through the object, said transmitter comprising a first hollow container that is slidably received in the main body and a ceramic transmitter resiliently mounted in said first container;

means urging said transmitter towards said object;

means to restrict the movement of said transmitter;

a piezoelectric ultrasonic receiver spaced from said transmitter and also projecting towards said body, said receiver comprising a second hollow container slidably received in said main body, and a ceramic transducer resiliently mounted in said second hollow container;

means to generate a signal to be transmitted; and means to amplify said received signal.

In one embodiment the main body includes a recess that receives the object. The means urging the transmitter towards the object then act to urge the transmitter into the recess in the main body.

Preferably the object is a foot.

DESCRIPTION OF THE PREFERRED EMBODIMENTS

Figure 1:
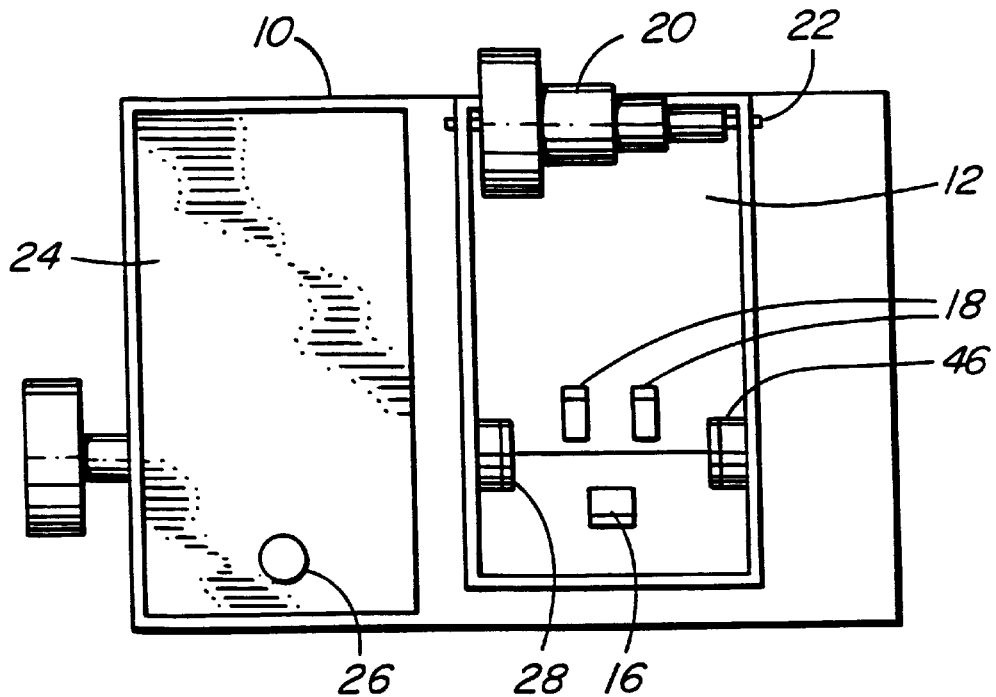
FIG. 1 is a plan view of an apparatus according to the present invention.

The drawings show an apparatus to measure the physical characteristics of an object. As shown particularly in FIGS. 1 and 2 the apparatus has a main body 10 that includes a recess 12 to receive the object 14, typically a foot as shown in Figure 1a. The apparatus includes means to determine when the object is correctly positioned in the recess. In the illustrated embodiment that means comprises a plurality of pressure sensors. There is a pressure receptor 16 to contact the heel, as shown in FIG. 1a, and a pair of pressure sensors 18 to contact under the heel, again as shown in FIG. 1a. The operation of these sensors is discussed subsequently, notably with regard to FIG. 5.

Figure 1A:
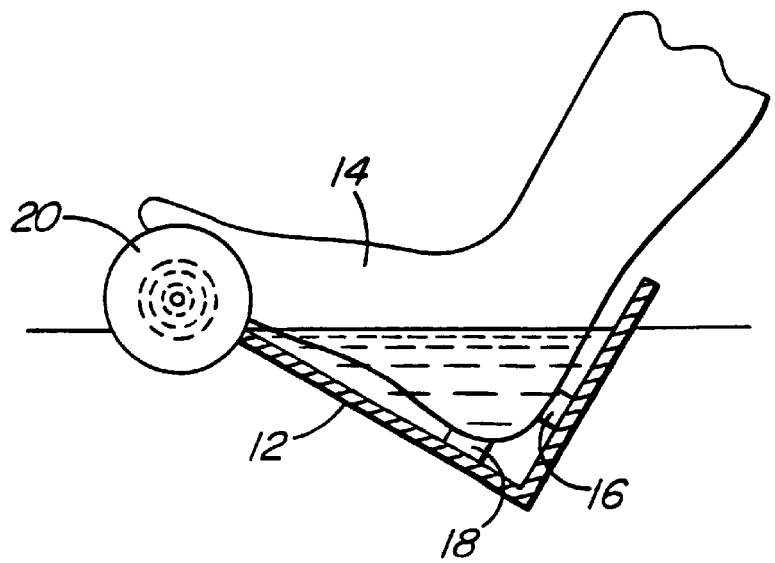
Figure 1a is a detail of FIG. 1.
Figure 2:
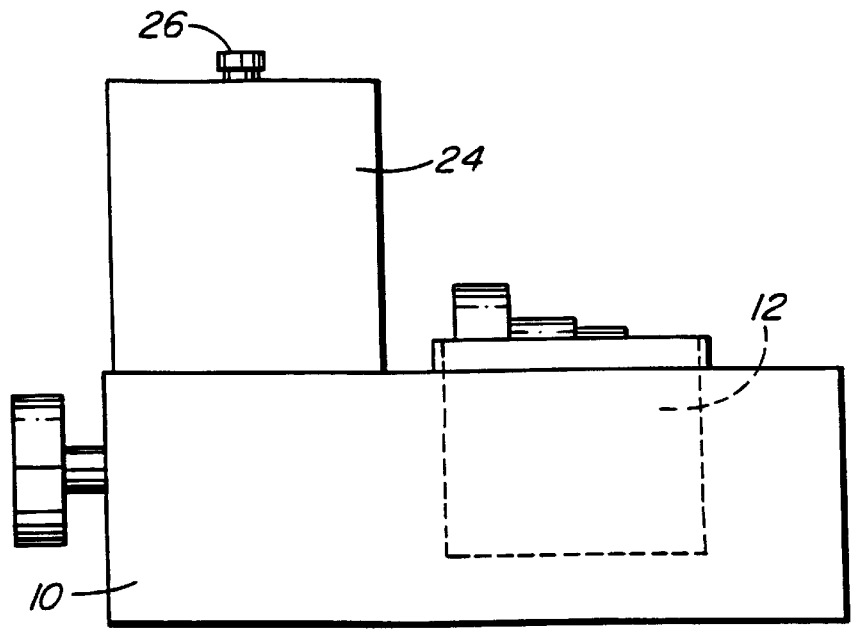
FIG. 2 is a side elevation of the apparatus of FIG. 1.

In addition the apparatus of FIG. 1 includes a toe stabilizer 20 also useful to determine the correct position of the object in the recess when the object is a foot 14. The toe stabilizer 20 is stepped and is received in that part of the recess 12 remote from the pressure sensors 16 and 18 for the heel of the foot. As shown particularly in Figure 1a the big toe of the user is placed against the toe stabilizer and the position thus achieved. It should be noted that the stabilizer is removably attached in the recess which means it can be used for either the left or the right foot. To facilitate removal stabilizer 20 includes a spring loaded mounting 22 shown in FIG. 1.

There is a reservoir 24, having a filling cap 26, to hold liquid to be used in the recess 12 during measurement. In this regard, however, it should be emphasized that the use of a fluid and, indeed, the use of a recess 12 to receive the fluid is not essential to the apparatus of the present invention. A virtue of the equipment, at least compared with applicant's own prior art, is that the fluid reservoir 24, the recess 12, and the heating of the fluid are not necessary in the apparatus of the present invention. A viscous liquid or gel may be interposed between the heel and the transducer. Other applications may necessitate the total immersion of the object to be measured, for example if the object has irregular surfaces.

The apparatus of the present invention as illustrated includes heating means 25 (see FIG. 5) to ensure that the liquid contained in the reservoir 24, and thus in the recess 12 during measurement, can be maintained at a temperature slightly above the temperature of the object being assessed. This prevents the formation of bubbles in liquids like water, which interfere with the reflecting ultrasound. Temperature is measured by a sensor 27.

Figure 4A:
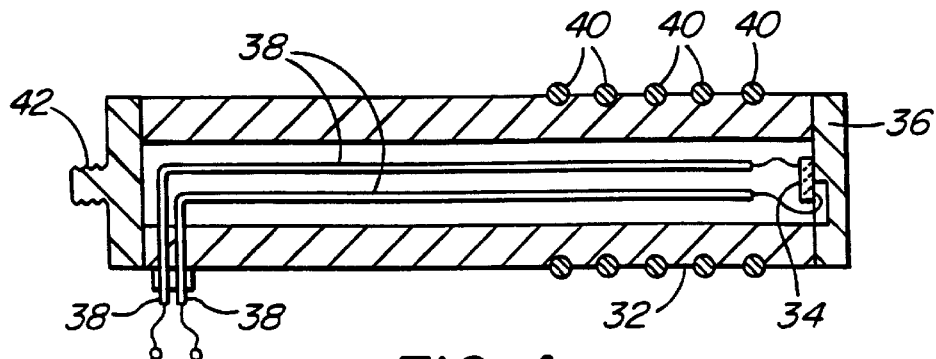
FIG. 4a is a detail view of an ultrasonic transmitter useful with the apparatus of the present invention.

There is a piezoelectric ultrasonic transmitter 28 to send a signal through the object 14. As shown particularly in FIGS. 3a, 3b and 4a the ultrasonic transmitter 28 comprises a first, hollow container 30 that is slidably received in a recess 32 in the main body 10. There is a ceramic transmitter 34, shown in FIG. 4, attached to a face plate 36 of the container 30. The container 32 includes connections 38 that extend to a pulse amplifier discussed below.

In addition the container 32 includes O-rings 40 located on its exterior to seal and also to facilitate movement of the container 32 within the main body 10. At its trailing end there is a stud 42 that allows attachment of the container 32 to a spring chamber 44, shown in FIG. 3b.

Figure 4B:
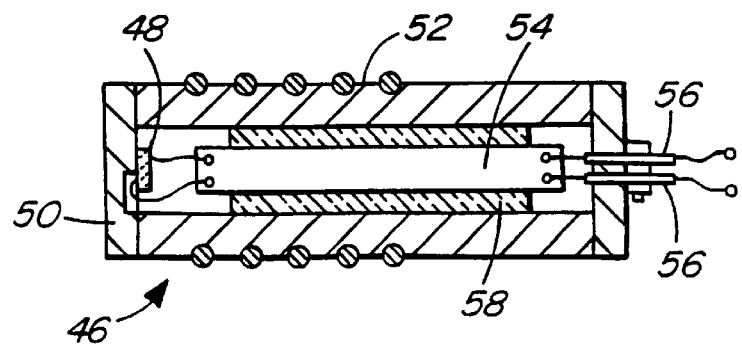
FIG. 4b is detail view of an ultrasonic receiver for use with the apparatus of the present invention.
Figure 3A:
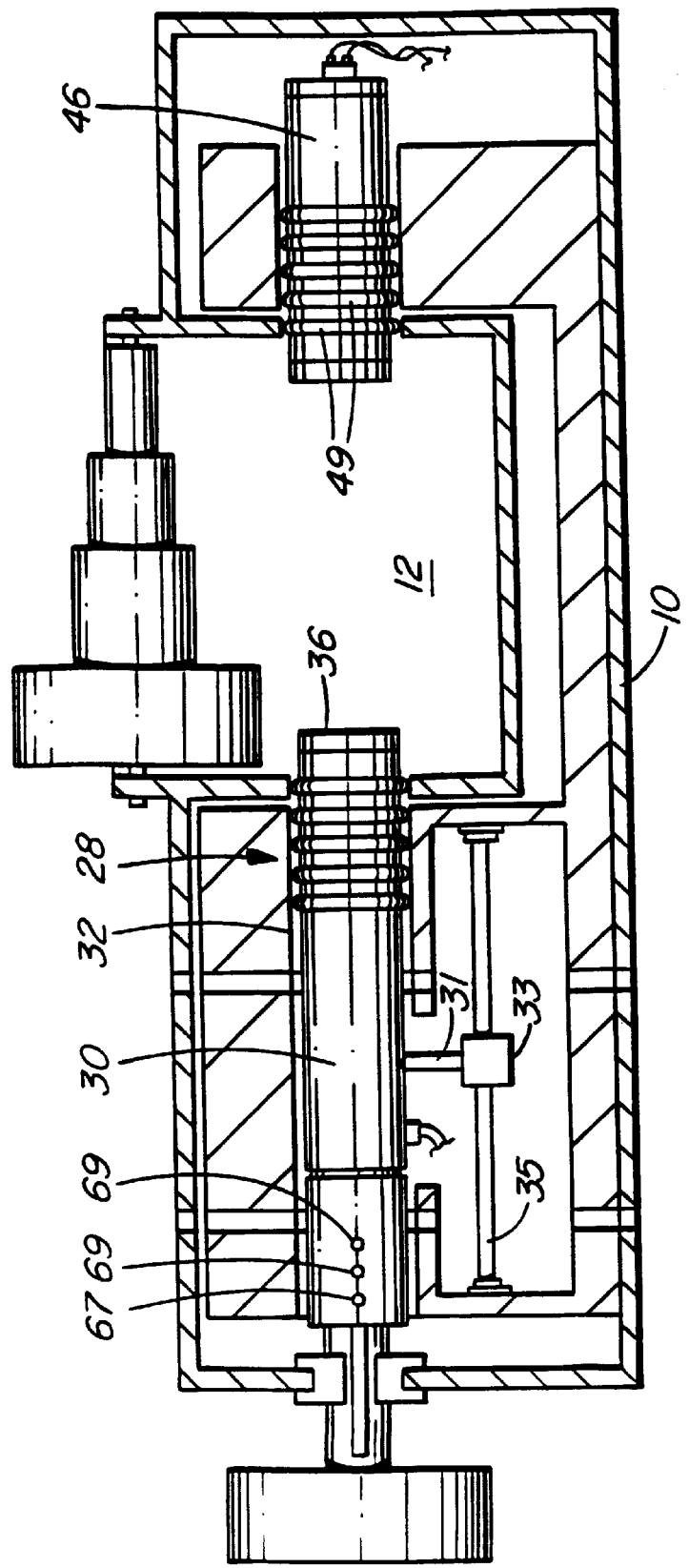
FIGS. 3a and 3b are further details of FIGS. 1 and 2.

The apparatus also includes a piezoelectric ultrasonic receiver 46, shown particularly in FIG. 3a, and 4b and spaced from the transmitter 28 across the recess 12. Like the container 30 of the transmitter 28 the receiver 46 also has O-rings 49 on its outer surface. The ultrasonic receiver 46 including transducer 48 mounted on an end plate 50 of a cylinder 52. O-rings 49 are around the exterior of the cylinder 52 and there is a preamplifier 54, attached to a micro processor through connection 56. There is also an insulating spacer 58 within the second cylinder 52.

Container 30 has a bolt 31 extending from it. A quill 33 is attached to bolt 31 and moves along an optical ruler 35. This is used to determine the position of the container 30 and thus of the transmitter 28.

In both the transmitter and the receiver, the face plates 36 and 50 are desirably resilient and the piezoelectric ultrasonic receiver and transmitter 34 and 48 are ceramic transducers, resiliently mounted. In a preferred embodiment the face plates 36 and 50 are of an adhesive sealant which functions as a resilient seal for the cylinder 32 and 52 and also acts as a supporting structure for the piezoelectric ceramics. In a preferred embodiment the face plates 36 and 50 also act as focusing devices for the equipment.

Figure 3B:
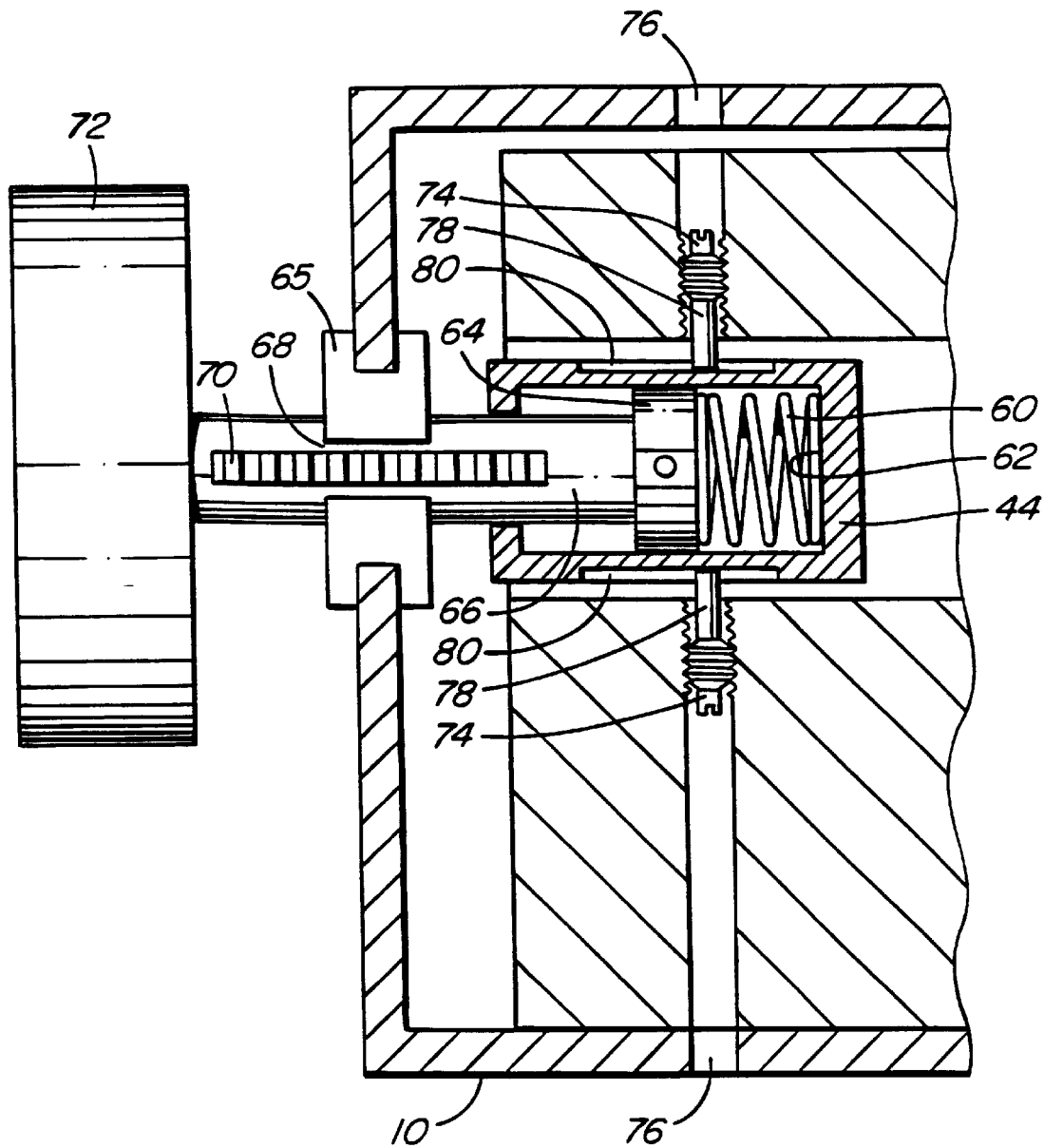

The ultrasonic transmitter 28 is urged into the recess 12 in the main body 10 by the provision of spring chamber 44 shown in FIG. 3b and including an internal spring 60. Spring chamber 44 has a threaded opening 62 that receives the stud 42 shown in FIG. 4a. The spring 60 abuts an end 62 of the third chamber 44 and a piston 64, mounted on a rod 66 that extends out of the third chamber 44. The piston acts to compress the spring 60. There are means to fix the position of the piston 64 and thus the tension of the spring 60 in the form of screws 67 that are received in holes 69 as best shown in FIG.3a. In an alternative arrangement illustrated in FIG. 3b, there is collar 65 mounted in the main body 10, and provided with engagement means, typically in the form of a recess 68. There are projections or engaging gears 70 on the rod 66 able to engage with the recess 68 in the collar 65. The rod 66 also has a handle 72 to allow rotation.

Using this equipment the rod 66 may be pushed inwardly, until the appropriate tension is achieved in the spring 60 and then rotated so that the engagement means 65 and 68 engage each other to fix the position of the piston 64 and thus the tension in the spring 60.

The tension of the spring 60 can be pre-set by the use of screws 74 that can be located through passageways 76 to be screwed inwardly to compress a nylon bearing 78 into channels 80 provided in the cylinder 44.

Figure 5:
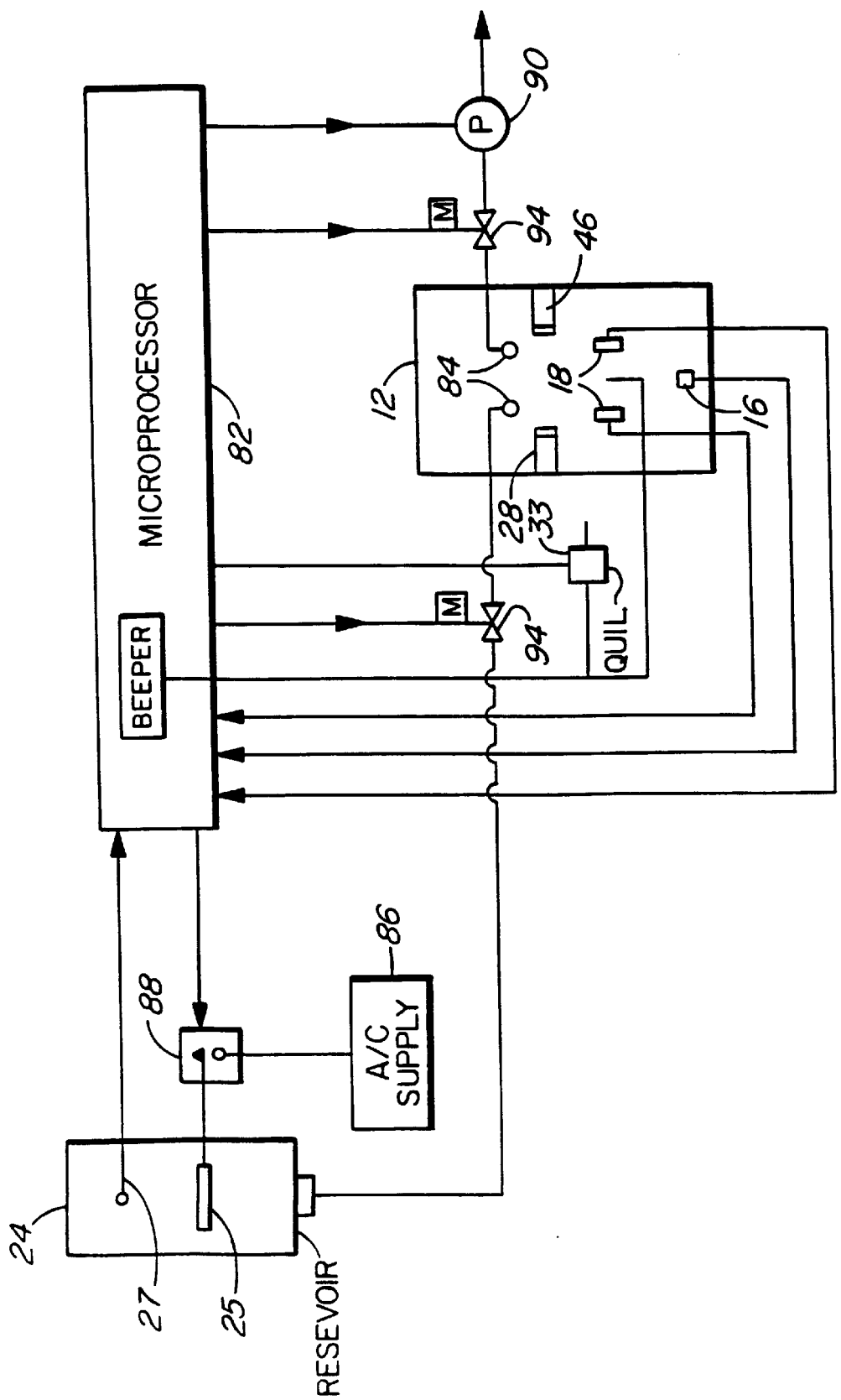
FIG. 5 shows schematically the apparatus for the present invention.

FIG. 5 shows the control of the equipment. There is a microprocessor 82 that receives signals from the pressure sensors 16 and 18 and acts to control filling and empty of the recess 12 through ports 84 and the temperature of the fluid in the recess. There is an alternating current supply 86 and an on/off relay 88 controlling the equipment.

The microprocessor 82 will ensure that the recess 12 is filled and emptied, using a pump 90 and the motorized valve 94 shown in FIGS. 5, according to a pre-set plan. The microprocessor 82 will ensure that the recess 12 will not be filled with liquid, usually water, at an undesirable temperature and will also ensure that the recess 12 is filled and drained as appropriate. It will also ensure that readings cannot be taken unless the heel is properly located. This is done by scanning the signals from the pressure sensors 16 and 18.

Information from the quill 33 is also stored in microprocessor 82.

Figure 6:
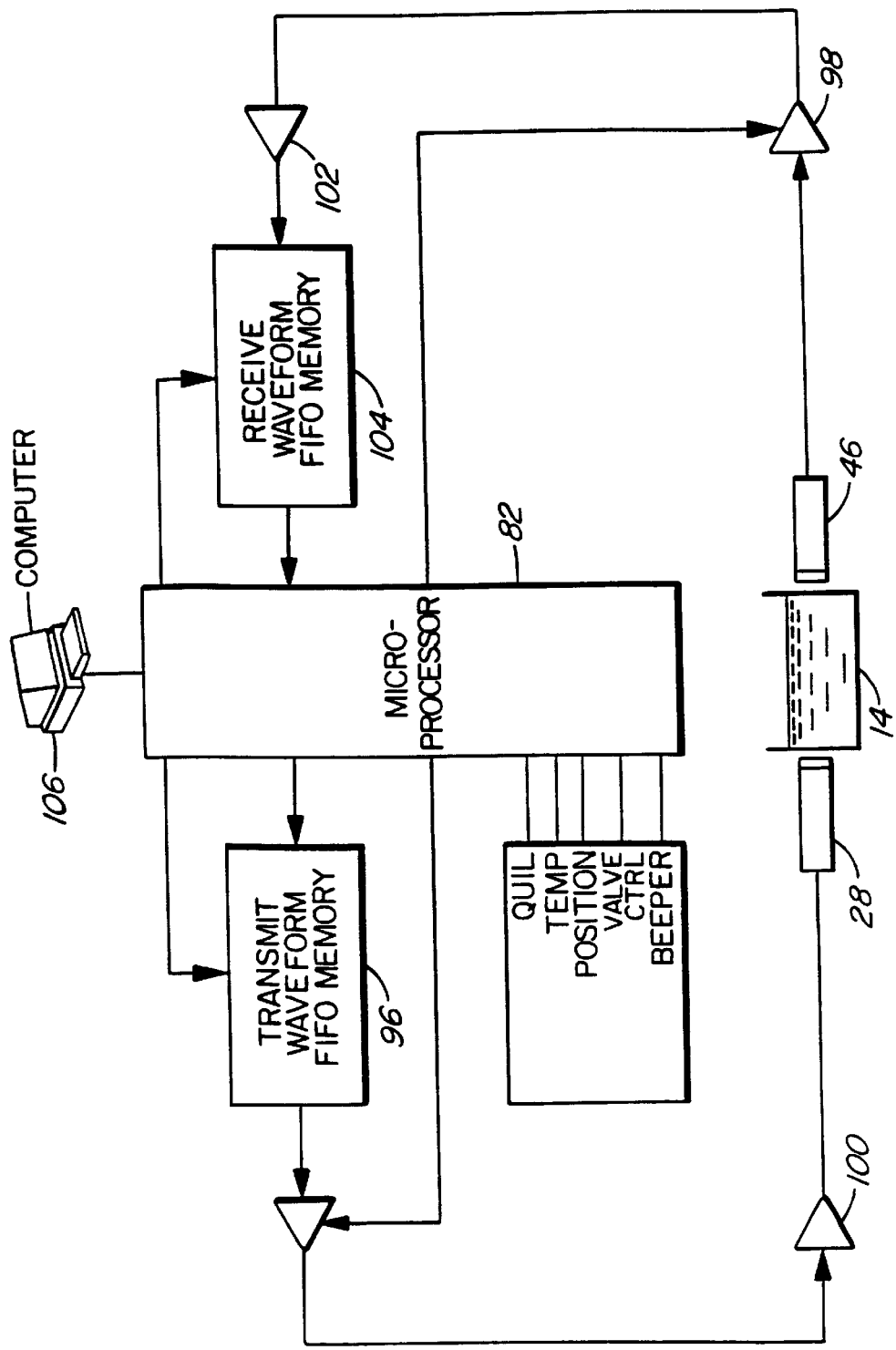
FIG. 6 illustrates the computer and control circuitry with signal transmission and processing.

FIG. 6 illustrates the control circuitry. The microprocessor 82 generates a digital representation of the desired transmit waveform into a transmit FiFo (first in first out) memory 96. The microprocessor 82 sets the gain of transmit digital/analog (D/A) and the gain at a receiver pre-amplifier 98. The microprocessor initiates wave form transmission from transmit Fifo 96 through the video D/A power amplifier 100 and the transmit transducer 28. Sound energy from the transmitter 28, having passed through the heel of foot-14, is detected by the receiving transducer 46 and the signal is amplified by the programmable gain pre-amplifier 98 digitized by the video A/D converter 102 and stored in the receiver FiFo memory 104. The microprocessor 82 then retrieves the received waveform from the receiver FiFo memory 104 and performs an analysis. The microprocessor 82 then sends the receive waveform for analysis to a personal computer 106 for storage and display.

To operate the equipment of the present invention as illustrated in the drawings, the microprocessor is programmed to automatically control the temperature, to fill up the empty bath, to record patient names and other data. All of this information is controlled as shown in FIG. 6. This is shown schematically as this software is well known.

The reservoir 24 is filled and the temperature in the reservoir raised sufficiently to yield a temperature at several degrees higher in the recess than the temperature of the object, typically a foot. The patient's foot is cleansed with detergent, rinsed and thoroughly dried. A small amount of a wetting agent is added to the reservoir. The heel is then placed in the bath 12 so that specified pressure is exerted against the back and sole part of the heel and this information relayed to the microprocessor by the pressure sensors 16 and 18. If the sole pressures, measured by the sole sensor 18 shown in FIG. 5, are unequal the knee is moved to the left or right to achieve equal pressure. This aligns the heel bone perpendicular to the transducers. The knee is maintained in the same position for the duration of the test.

Knob 72 with the off position showing vertically, is pushed until the preset contact pressure against the heel is achieved. The knob 72 is then rotated until the on position is vertical, that is to say the rod 66 is locked within the collar. This enables the retainer screws to hold the spring 60 in a compressed position. The receiver piezoelectric element and associated mechanical mounting allow the receiver to vibrate freely with a minimum of energy lost to the casing. In this configuration the transducers exhibit two strong resonant frequencies, 171,400 Hz and 668,400 Hz. The predominant receiver frequency is the former 171,400 Hz. The effect of these freely resonating frequencies is that when the receiver is impacted with a small amount of ultrasonic energy, or at the end of receiving a large amount of ultrasonic energy, the receiver exhibits a strong tendency to vibrate 171,400 Hz. The strength of this tendency is directly dependent upon a constant which is the modulus of elasticity of the ceramic material. Thus the material does not need calibration or reference standard. These receiver characteristics and resonant frequencies are used to advantage in determining bone integrity in the following way.

If the transmitter produces, say, two cycles (sinusoidal) of ultrasound at 668,400 Hz the receiver will begin vibrating at 668,400 Hz and then transition to vibrating at 171,400 Hz will take place until the vibrations end. The energy expended by the receiver vibrating at 668,400 Hz versus the energy vibrating at 171,400 Hz depends on the amplitude of the received ultrasound which, in turn, depends on the energy absorbed by the heel. When the signal arrives at the receiver the microprocessor performs a predetermined gain adjustment on the programmable gain preamplifier according to the scheme of FIG. 6. This produces a trace of sufficient magnitude for accurate analysis. As the amplitude of the trace for analysis is thus increased or decreased to a predetermined amplitude, it can be said that it is independent of the density or thickness of the heel bone. Therefore it is known that as humans age they lose density. However the loss of structure is a serious event that could lead to fracture. Thus in this method good bone quality could have the same value at 65 as at 25 years of age, unlike bone density, which decreases with age.

A useful measure of bone integrity has been achieved by spectral analysis of the above received waveform between 80 KHz and 245 KHz, the low frequency and between 245 KHz and 860 KHz for the high frequency component and forming a % ratio according to the formula:

$$\text{T-index} = \left[\frac{\text{Area of High Frequency Component}}{\text{Area of Entire trace}} \times 100\right] - 100 = \%.$$

This equation yields a new type of index, termed the trabecular or t-index of osteoporosis that is easily interpreted. In general a t-index value of 80% to 90% represents healthy bone. Decreasing values below 80% correlate with increasing structural problems. Values as low as 30% have been found in bone having structural problems leading to fracture. As the structural integrity is measured this test can differentiate between osteomalacia and osteoporosis as the integrity of the structure is affected in the latter but not in the former.

An alternative method according to the present invention eliminates the need for spectral analysis. According to this alternative method the transmitter produces, say, a 2 cycle Sinewave burst of ultrasound at 668,400 Hz and the trace is recorded. A second trace of a single cycle is generated at 171,400 Hz and the amplitude adjusted so that the received waveform is the same amplitude as the original waveform. Now the two waveforms can be matched in time so that a minimum difference waveform is obtained. The area of the difference of the waveform is the high frequency component in the ratio above and the area of the second waveform is a total area of the same ratio. This method eliminates the complex spectral analysis and attains a higher lever of accuracy.

In addition to providing a structured integrated value, the apparatus of the present invention can measure bone density and the velocity of sound in bone. Although the density and velocity do not detect the initial stages of osteoporosis they do provide an indication of how advanced the disease is. Unlike the trabecular (structural) index measurement, the density and velocity measurements require a heel width measurement. The quill 33 shown in the drawings records the horizontal movement of the transmitting transducer 28. The quill 33 is zeroed by inserting a known width gauge between the transducers 28 and 46. This width is inserted into the program and added to subsequent measurements by the quill 33.

The rationale for measuring bone density is as follows:

It has been observed that the low frequency wave (say 171400 Hz) passes through the heel bone with very little difference in attenuation from person to person. Whereas a much higher frequency wave (say 668,400 Hz) shows large attenuation differences from person to person. These observations enable a self-calibrating method for measuring bone density as follows. A number of measurements are performed on a single individual preferably a healthy male. These measurements consist of recording the voltages necessary to transmit at a low frequency (171,400 Hz) and obtain 180 units of amplitude on the recorder. The lowest value obtained represents optimum coupling between the transducers and the heel. This voltage value is inserted into the program and is referred to as the low frequency normalization factor (L.F.N.F.) and used in the density measurements for all patients.

In operation the heel is maintained in position and the voltages needed to achieve 180 units at the recorder for the low and high frequency pulse (171,400 Hz) are increased or decreased by the microprocessor and the calculation of density computed as follows:

$$\text{Density} = \frac{\text{L.F.N.F. Amplitude (volt)}}{\text{Low Frequency Amplitude (volts)}} \times \frac{\text{High Frequency Amplitude (volt)}}{\text{Heel Width (mm)}}$$

Density = Volts/Millimeter (Units)

Density =

$$\% \text{ of normal young adult value} = \frac{\text{Patient Value}}{\text{Normal Young Adult Value}} \times 100$$

The present device measures bone density more accurately than previous devices because no phantom (reference standard) is needed. Further the degree of coupling between the test object and the transducers is not a source of error as the L.F.N.F. makes a correction for this.

The position of the foot is maintained for the velocity measurement. By recording the time interval for the pulse to travel through the heel and dividing the heel width by this time the velocity is determined in meters/second. The high frequency trace (668,400 Hz) is used to note the time of arrival of the pulse. This is difficult for the computer to detect as the beginning of the trace is ill-defined. The trace is amplified by the preamplifier enabling the beginning of the trace to be detected by the human eye. The computer easily measures the time of second crossing of the base line as displayed on a monitor. That time interval is measured and has been found to be relatively constant for all patients at 2.026 microseconds. As the computer can easily detect the second crossing of the baseline of the trace used for analysis the above constant value of 2.026 is subtracted from the value to provide the precise time of arrival of the pulse. Other than this unique feature of ensuring that the time is measured with extreme accuracy, the velocity method and its use in evaluating bone is well documented and will not be further elaborated on.

Unlike any other device, this method provides the measurement of three parameters of bone quality, namely structural integrity, bone density and velocity of sound in bone. This enables early detection of osteoporosis and evaluates the therapeutic procedures to correct the condition.

Although the invention describes particularly the use of the method and apparatus to diagnose osteoporosis the apparatus and method can be directly applied to process control in the process industries—food, pulp and paper, petrochemical, pharmaceutical, paint, dairy etc.

EXAMPLES

Pulp and Paper Industry

The "t-index" above may be used to indicate the amount of water in the pulp when flowing or in a fixed sample (See FIG. 7). The higher the pulp to water ratio the higher will be the "t-index".

EXAMPLE

Solids content in the Food Industry

The higher the particulate in a liquid the higher the "t-index".

EXAMPLE

Density Measurements

The value of density measurements throughout industry is well documented. However, the ultrasonic methods used are not as accurate as the method of the present invention.

In other applications, a higher intensity of sound may be needed. In this case the transducer face plate of adhesive sealant is shaped to achieve the desired focusing of the sound beam as shown in FIG. 7. If the higher intensity is insufficient the receiving and transmitting transducers may be brought closer together by rotating them clockwise, assuming the body of the transducer has a right hand thread. In all applications two resonating frequencies are utilized—a higher and a lower frequency achieved by having piezoelectric ceramics operating in the thickness and radial mode and mounted so as to minimize the damping.

Although the above method and apparatus are described particularly in relation to diagnosis of osteoporosis it can also be used to distinguish between osteomalacia and osteoporosis and can also be directly applied to process control in industry, for example in the food, pulp and paper, petro chemical, pharmaceutical, paint and dairy industries. Assuming the application is pulp and paper, one application in this industry is to determine the amount of water in a slurry of pulp. The higher the pulp to water ratio the higher will be the index as discussed above. Both the spectral analysis and the different curve will provide the information.

Figure 7A:
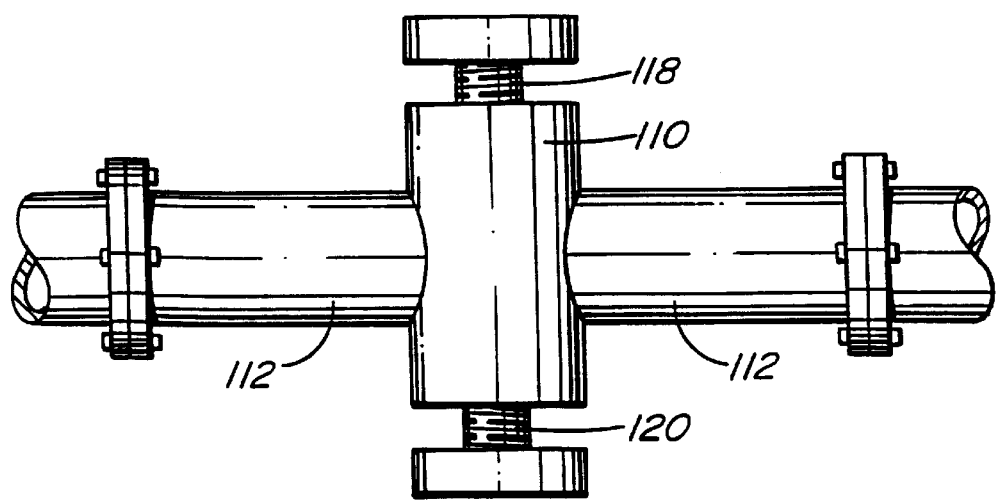
FIGS. 7a, 7b and 7c are general views is a general view of the transducers used in the apparatus of the present invention.
Figure 7B:
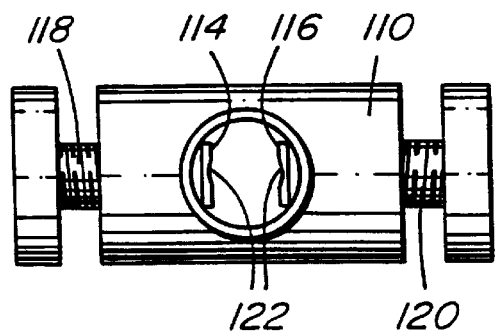
Figure 7C:
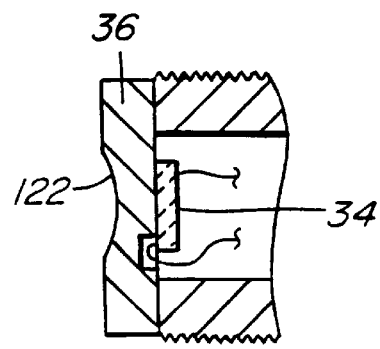

Apparatus to enable the determination of this is shown in FIGS. 7a, 7b and 7c where a simple container 110 is installed in a pipeline 112 in which a transmitter 114 and a receiver 116 are mounted on threaded, sealed member. The necessary signals are taken and interpreted as shown in FIG. 6. The relevant equipment is not shown in FIG. 7. Here is a particular example of the face plates acting as focusing members and to that end they are provided with concave recesses 122.

In other applications a high intensity of sound may be needed. In this case a transducer face plate is shaped to achieve the desired focusing of the sound, as shown in FIG. 7b. If the high intensity is not attained the receiving and transmitting transducers may be brought closer together by rotating them clockwise on the threads. The resonating frequencies are always used—and a higher and a lower frequency by having the ceramics operate in the thickness and radial mode respectively.

This aspect of the invention is of extreme importance. For efficient transfer of power from the generator to the medium the two must be acoustically matched. The specific impedance of the ceramic is approximately 30 mRayls and that of water is 1.5 mRayls, there is a need to smooth out the discontinuity so that the transfer of energy from the transducers to the medium is maximized. A layer of a material with an acoustics impedance intermediate between the ceramic and water, by being interposed between the two, provides good matching using polymers with impedances of about 3.5 mRayls. These are readably available. The velocity of sound in these are approximately 2400 metres per second so the thickness required will vary with the frequency used.

Both transducers are air backed. The transmitter is made of a material of 5400 Navy (U.S.A.) whereas the receiver is 5500 Navy (U.S.A.). The diameters of both on 0.5 inches and the thicknesses of both are 0.1 inches. The main body of the transducers should have an outside diameter of about 1 inch and an inner diameter of about 0.6 inches. As the ceramic is only 0.5 inches compression of the ceramic between the body and the object to be measured is prevented. It is only the face plate that is compressed between the object and the main body. The characteristic of the sealant is such that it possesses strong adhesion and remains pliable and is a non-conductor of electrical current. A preferred material for this use is that available under the trademark E 6000 from Eclectic Products, which is a styrene based adhesive sealant. The combined effect of the sealant and the transducer ceramic geometry, that is 5 to 1 ratio of diameter to thickness, disc shape and ceramic mounting techniques allow both transducers to resonate in both the radial and thickness modes. This provides a low resonating frequency in the radial mode and a high resonating frequency in the thickness mode of vibration. This method of mounting ceramic and using a compliant or resilient face plate not only produces a highly efficient transducer but enables production of piezoelectric transducers that have virtually the same characteristics. The geometry of the transducers is such that the radial mode is preferred. That is if a single burst of energy, of the higher resonating frequency is received by the receiver it will start vibrating at this higher frequency, in the thickness mode and change into the radial mode, proportional to the energy of the burst received. That is to say the length of time spent in the thickness mode is proportional to the energy of the burst received. This competition between radial and thickness modes of vibration is based upon the modulus of elasticity of the ceramic and provides its own reference as the modulus of elasticity is a constant, thus avoiding the necessity for calibration.

Although the present invention has been described in some detail by way of example for purposes of clarity and understanding, it will be apparent that certain changes and modifications may be practised within the scope of the appended claims.

I claim:

1. An ultrasound apparatus for making ultrasonic measurements of an object comprising:

a transmitting ultrasonic transducer for generating ultrasound energy pulses;

a receiving ultrasonic transducer to receive the energy pulses from the transmitting transducer;

the transmitting and receiving transducers being spaced apart to receive the object therebetween with each of the transmitting and receiving transducers having a radial axis and a longitudinal axis and being resiliently mounted such that the transducers are free to oscillate radially and axially in response to energy pulses and exhibit at least two resonant frequencies; and means for analyzing the energy pulses received by the receiving transducer after transmission through the object to make ultrasonic measurements of the object.

2. An ultrasound apparatus as claimed in claim 1 in including spaced, co-axial hollow bodies having sealed, resilient end surfaces with the transmitting and receiving transducer being mounted to the end surfaces of the hollow bodies.

3. An ultrasound apparatus as claimed in claim 2 which each of the transmitting and receiving transducers is a ceramic transducer in the shape of disc having two faces and diameter approximately 5 times greater than its thickness with one of the faces of the disc being attached to the end surface of the hollow body.

4. An ultrasound apparatus as claimed in claim 2 in which the end surfaces of the hollow bodies are formed to a pre-determined shape to focus the ultrasound energy pulses.

5. An ultrasound apparatus as claimed in claim 2 in which the end surfaces have the following characteristics:

i) strong adhesion to the transducer and the hollow body;

ii) inert to caustics, acids, and oils;

iii) mouldable; and iv) electrically non-conductive.

6. An ultrasound apparatus as claimed in claim 5 in which the end surface is formed from a styrene based polymer.

7. An ultrasound apparatus as claimed in claim 5 in which the object is a human body part and the end surface has an acoustic impedance between that of the transducer and human tissue.

8. An ultrasound apparatus as claimed in claim 2 including:

a housing to slidably receive the transmitting and receiving transducer mounted in the hollow bodies and to receive the object;

means to determine when the object is correctly on the housing;

means urging the transmitting transducer towards the object; and means to restrict the movement of the transmitting transducer.

9. An ultrasound apparatus as claimed in claim 40 including a recess in the housing to receive the object.

10. An ultrasound apparatus as claimed in claim 9 in which the means to determine when the object is correctly positioned comprises:

a first pressure sensor in the recess to contact the under side of the object; and a second pressure sensor in the recess to contact the rear of the object; and means to generate a signal when pressure is correctly applied to the first and second sensors.

11. An ultrasound apparatus as claimed in claim 10 in which there are two first sensors.

12. An ultrasound apparatus as claimed in claim 10 in which, when the object is a foot, the means to determine when the object is correctly positioned includes a toe stabilizer mounted in the recess to abut a side of the toe to ensure the foot is in the correct position.

13. An ultrasound apparatus as claimed in claim 12 in which the toe stabilizer is stepped for variable size feet.

14. An ultrasound apparatus as claimed in claim 12 in which the toe stabilizer is reversible for use with both left and right feet.

15. An ultrasound apparatus as claimed in claim 9 in which the means urging the transmitting transducer toward the object comprises a spring mounted in a third body attached to the hollow body containing the transmitting transducer.

16. An ultrasound apparatus as claimed in claim 15 in which the spring abuts an end of the third body; and the third body includes a piston to abut the spring to compress the spring; and means to fix the position of the piston and thus the tension of the spring.

17. An ultrasound apparatus as claimed in claim 16 in which the piston is mounted on a rod that extends out of the third body and out of the housing;

a collar on the housing having first engagement means;
second engagement means on the rod, engageable with the first engagement means whereby rotation of the rod acts to release an engage the first and second engagement means.

\* \* \* \* \*